United States Patent
Patterson-Young

(10) Patent No.: US 8,608,718 B1
(45) Date of Patent: Dec. 17, 2013

(54) URINE COLLECTION BAG HOLDER

(76) Inventor: Angela A. Patterson-Young, Harker Heights, TX (US)

( * ) Notice: Subject to any disclaimer, the term of this patent is extended or adjusted under 35 U.S.C. 154(b) by 176 days.

(21) Appl. No.: 13/171,351

(22) Filed: Jun. 28, 2011

(51) Int. Cl.
*A61F 5/457* (2006.01)

(52) U.S. Cl.
USPC .......................................... 604/353; 604/345

(58) Field of Classification Search
USPC ................... 604/326–327, 345, 353
See application file for complete search history.

(56) References Cited

U.S. PATENT DOCUMENTS

| | | | | |
|---|---|---|---|---|
| 1,705,194 A * | 3/1929 | Marinsky | 604/400 |
| 2,699,782 A * | 1/1955 | Chester | 604/353 |
| 3,570,490 A * | 3/1971 | Berger | 604/332 |
| 3,897,785 A * | 8/1975 | Barto, Jr. | 604/327 |
| 4,122,851 A * | 10/1978 | Grossner | 604/347 |
| 4,173,979 A | 11/1979 | Odis | |
| 4,511,358 A * | 4/1985 | Johnson et al. | 604/327 |
| 4,705,512 A * | 11/1987 | Faucher | 604/332 |
| 4,874,387 A * | 10/1989 | Boone | 604/326 |
| 4,955,879 A * | 9/1990 | Mervine | 604/327 |
| 5,026,362 A | 6/1991 | Willett | |
| 5,032,118 A * | 7/1991 | Mason | 604/349 |
| 5,087,251 A * | 2/1992 | Heyman et al. | 604/327 |
| 5,193,553 A * | 3/1993 | Kalinoski | 600/580 |
| 5,234,420 A * | 8/1993 | Horton et al. | 604/345 |
| 5,259,541 A * | 11/1993 | Reese | 224/663 |
| 5,643,233 A * | 7/1997 | Turner | 604/332 |
| 5,643,236 A * | 7/1997 | Hadley | 604/353 |
| D395,356 S * | 6/1998 | Tang | D3/327 |
| 6,273,872 B1 * | 8/2001 | Friedman | 604/174 |
| 6,599,278 B1 * | 7/2003 | Nichols | 604/345 |
| 7,517,340 B2 * | 4/2009 | Barrientos | 604/353 |
| 7,691,091 B1 | 4/2010 | Baggett | |
| 8,092,436 B2 * | 1/2012 | Christensen | 604/318 |
| 8,348,914 B2 * | 1/2013 | Zyburt et al. | 604/317 |
| 8,361,044 B2 * | 1/2013 | Marshall | 604/327 |
| 2002/0010445 A1 * | 1/2002 | Gunn | 604/345 |
| 2004/0204695 A1 * | 10/2004 | Bisbee | 604/349 |
| 2006/0293631 A1 * | 12/2006 | Bolt | 604/353 |
| 2007/0208314 A1 * | 9/2007 | Barrientos | 604/353 |
| 2007/0260208 A1 * | 11/2007 | May | 604/345 |
| 2008/0140034 A1 * | 6/2008 | Edling | 604/327 |
| 2008/0269700 A1 * | 10/2008 | O'Toole et al. | 604/332 |
| 2009/0234310 A1 * | 9/2009 | Marshall | 604/327 |

* cited by examiner

*Primary Examiner* — Melanie Hand
*Assistant Examiner* — Paula Craig

(57) ABSTRACT

A urine collection bag holder including a fabric strip having a hip portion and a leg portion depending therefrom and a pouch removably attached to the leg portion wherein the pouch receives a urine collection bag therein, in order to conceal the urine collection bag beneath a user's clothes. A belt that slidingly engages a continuous belt opening within the hip portion and a pair of leg straps secure the device to a user. A plurality of slits and a tube opening disposed in the leg portion receive and guide a cathether tube therethrough to connect with an upper receptacle.

4 Claims, 4 Drawing Sheets

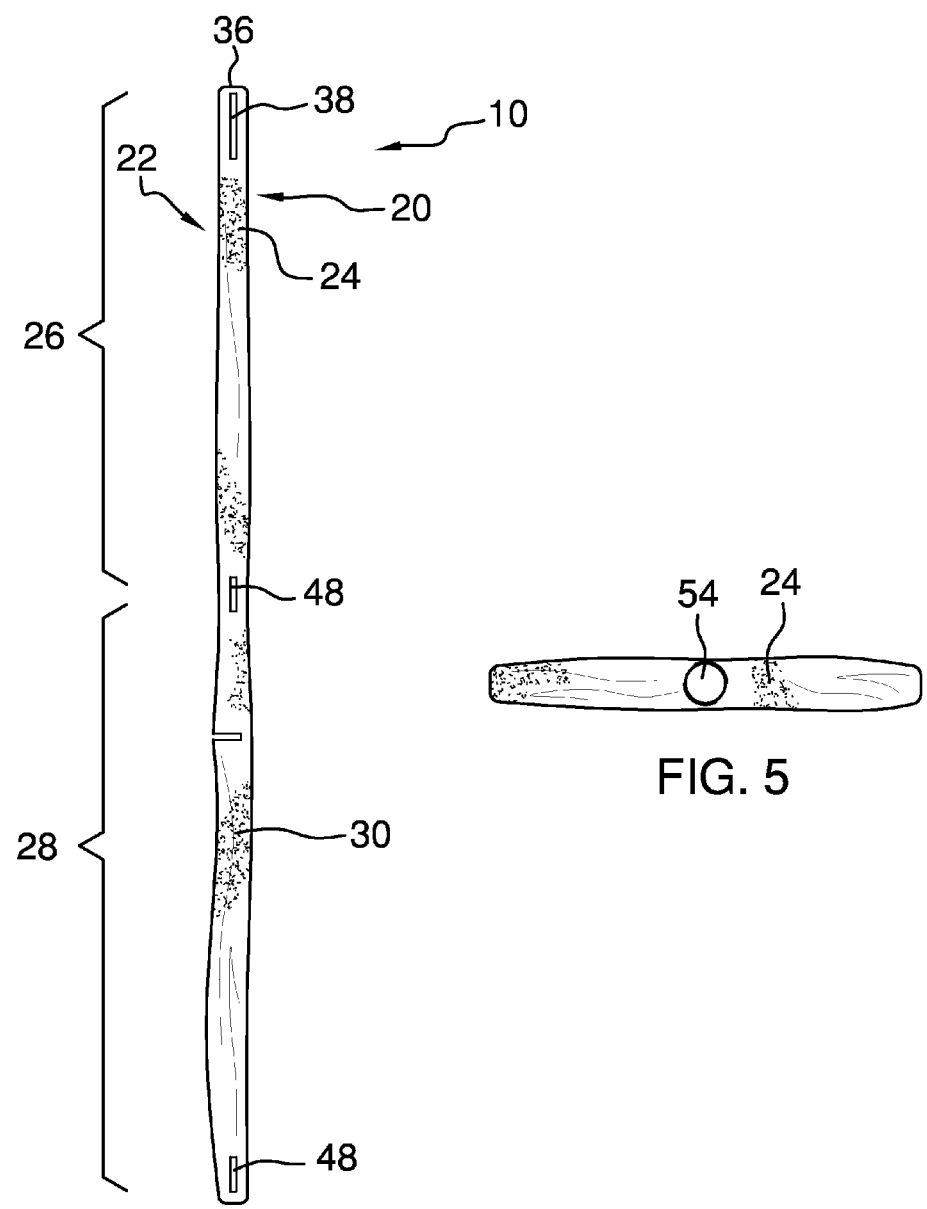

URINE COLLECTION BAG HOLDER

BACKGROUND OF THE INVENTION

Various types of urine collection bag holders are known in the prior art. However, what is needed is a urine collection bag holder that includes a fabric strip with a pouch disposed upon a leg portion, the pouch configured to receive a urine collection bag, which urine collection bag is thereby comfortably concealed beneath a user's clothes.

FIELD OF THE INVENTION

The present invention relates to a urine collection bag holder, and more particularly, to a urine collection bag holder including a fabric strip with a pouch disposed upon a leg portion, the pouch configured to receive a urine collection bag, which urine collection bag is thereby comfortably concealed beneath a user's clothes.

SUMMARY OF THE INVENTION

The general purpose of the urine collection bag holder, described subsequently in greater detail, is to provide a urine collection bag holder which has many novel features that result in a urine collection bag holder which is not anticipated, rendered obvious, suggested, or even implied by prior art, either alone or in combination thereof.

Many patients know the discomfort caused when wearing a urine collection bag. Urine collection bags are typically fashioned from plastic material, which material is impervious to perspiration when in contact with the skin. Urine collection bags therefore are known to cause chafing and irritation of the skin of the person using the urine collection bag. Urine collection bags also have a poor aesthetic, crafted for functionality rather than appearance. This makes urine collection bags unattractive and even stigmatized.

What is needed is a urine collection bag holder devised to comfortably conceal a urine collection bag beneath a user's clothing, the holder further devised to be more attractive than the clinical urine collection bag or holders typical of the prior art. The present device includes a fabric strip configured to be comfortable when in contact with the skin. The fabric will have designs rendered thereupon, improving the aesthetic of the urine collection bag holder for the user and others who may see the urine collection bag holder.

The fabric strip has a hip portion and a leg portion. The hip portion attaches to a belt threaded through a belt opening in the holder and hangs against the user's hip. The leg portion depends from the hip portion and is secured by a pair of lag straps to the user's thigh. A pouch is disposed on the leg portion, the pouch configured to receive a urine collection bag therein.

Vertical slits disposed within the hip portion directs a urine collection tube to connect with the urine collection bag through a tube opening disposed on the leg portion. Urine is thusly collected in the urine collection bag beneath a user's clothes, and the fabric strip ensures a comfortable situation to wearing the urine collection bag holder and carrying the urine collection bag. The urine collection bag holder further improves the aesthetic of the urine collection bag.

Thus has been broadly outlined the more important features of the present urine collection bag holder so that the detailed description thereof that follows may be better understood and in order that the present contribution to the art may be better appreciated.

Objects of the present urine collection bag holder, along with various novel features that characterize the invention are particularly pointed out in the claims forming a part of this disclosure. For better understanding of the urine collection bag holder, its operating advantages and specific objects attained by its uses, refer to the accompanying drawings and description.

BRIEF DESCRIPTION OF THE DRAWINGS

Figures

FIG. 4 is a side view.
FIG. 5 is a bottom view.

DETAILED DESCRIPTION OF THE DRAWINGS

Figure 1:
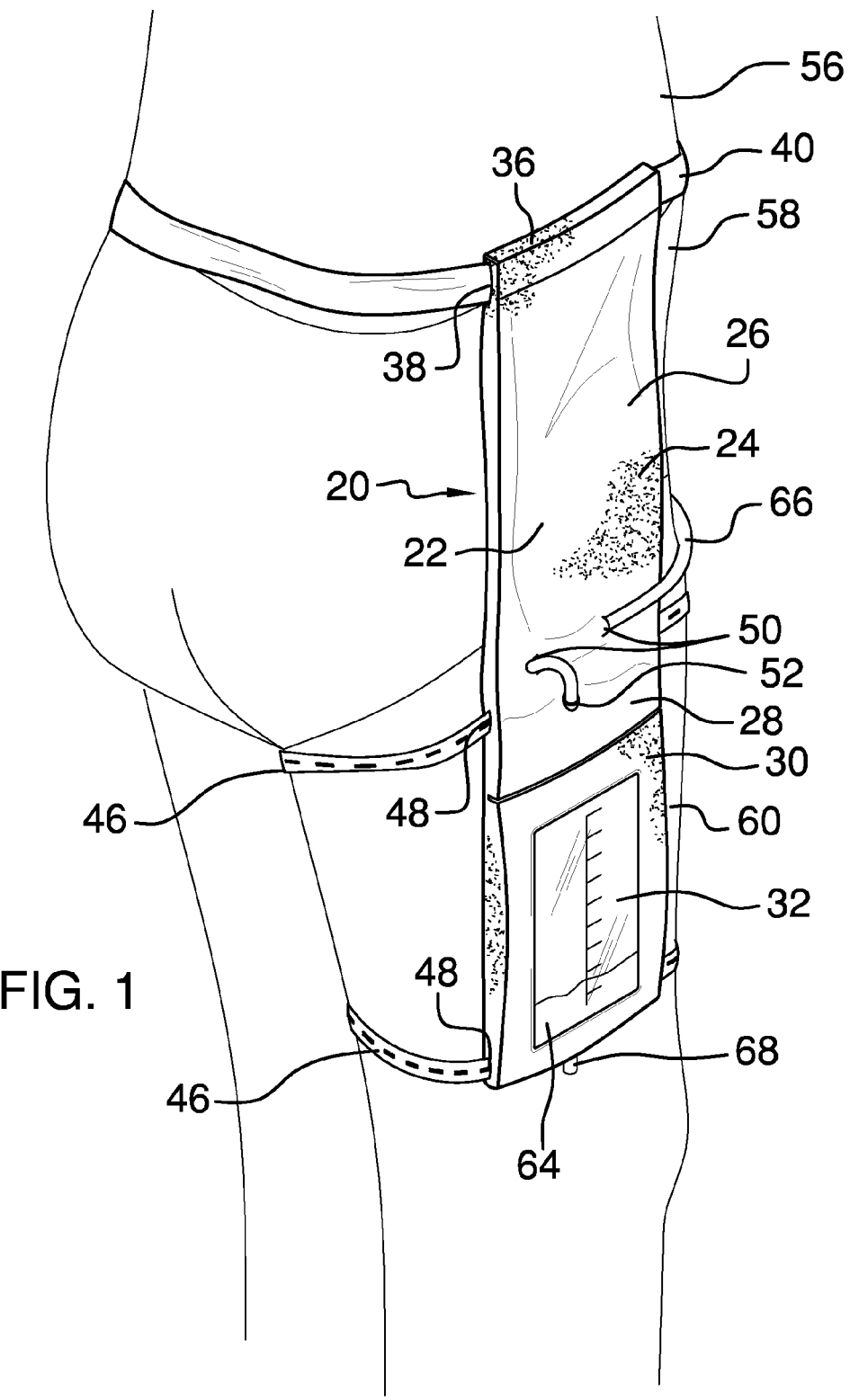
FIG. 1 is an in-use view.
Figure 2:
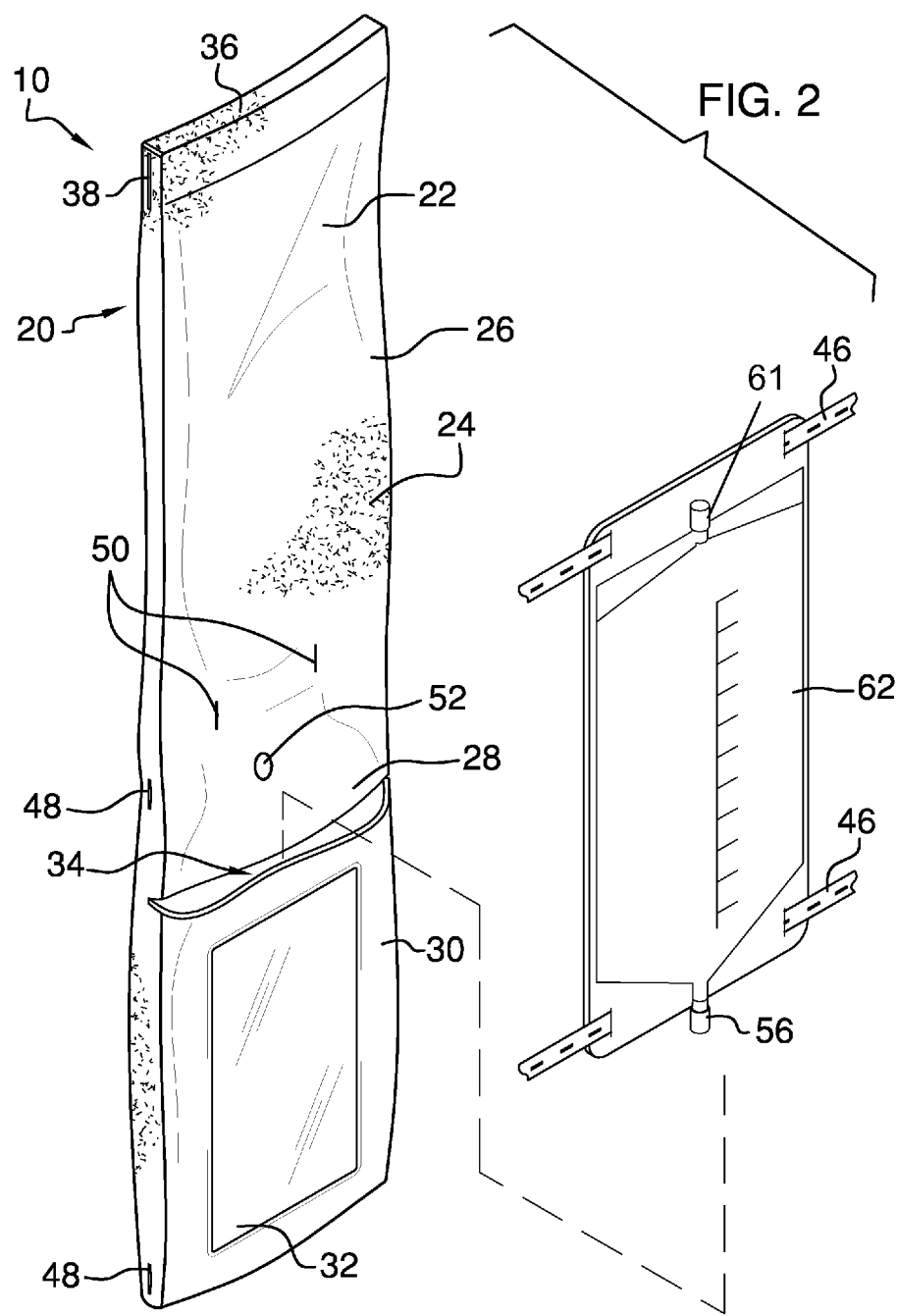
FIG. 2 is an exploded view.
Figure 3:
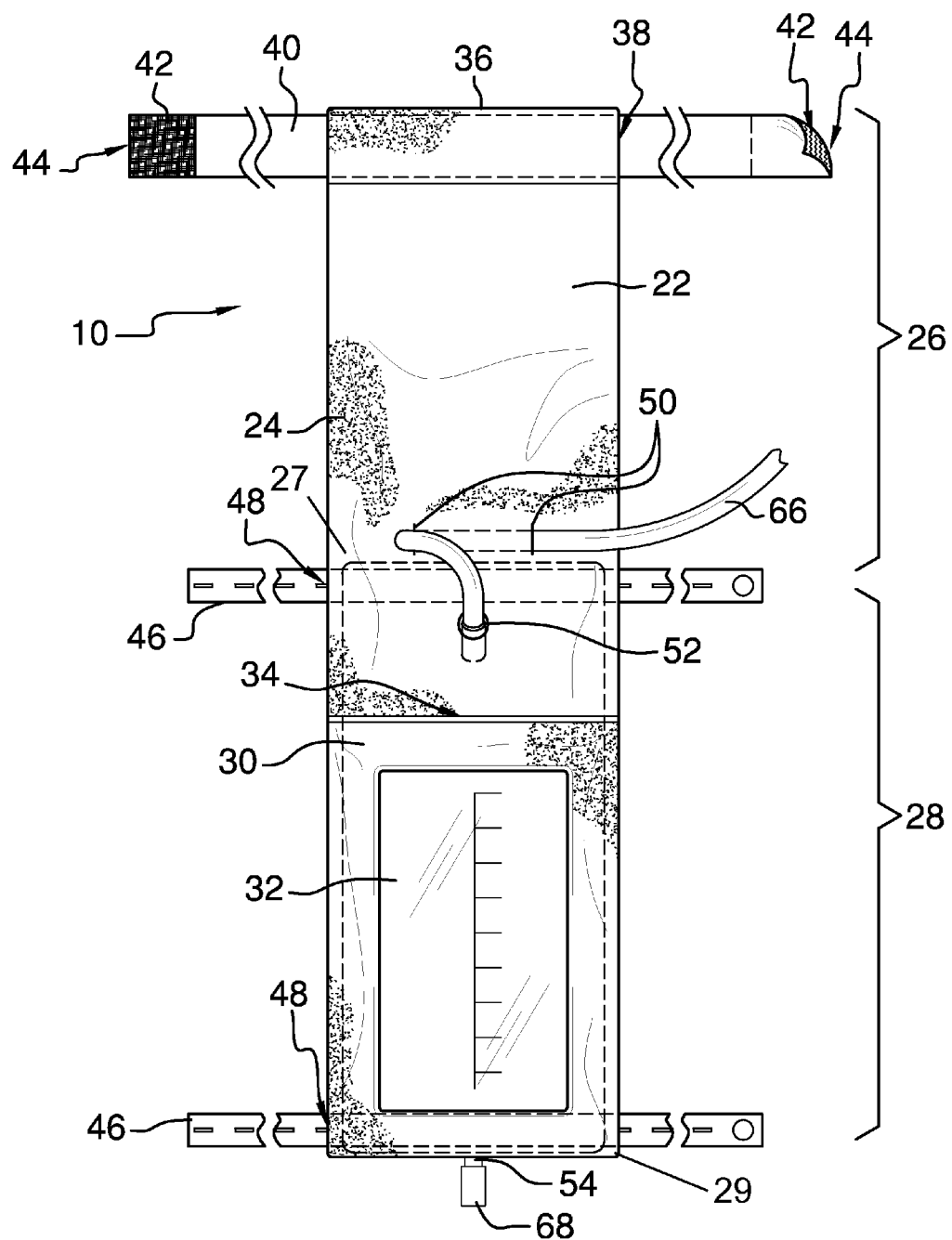
FIG. 3 is a front view.

With reference now to the drawings, and in particular FIGS. 1 through 5 thereof, example of the instant urine collection bag holder employing the principles and concepts of the present urine collection bag holder and generally designated by the reference number 10 will be described.

Referring to FIGS. 1 through 5 a preferred embodiment of the present urine collection bag holder 10 is illustrated.

A generally rectangular urine collection bag holder 10 includes an inside surface 20 and an outside surface 22. The inside surface 20 is disposed next to the user 56 when the urine collection bag holder 10 is worn. It is envisioned that the urine collection bag holder 10 will be made of a soft fabric 24 to lessen chafing and discomfort when the urine collection bag holder 10 is worn. The fabric 24 will have designs rendered thereupon to improve the aesthetic of the urine collection bag holder 10.

The urine collection bag holder 10 also includes a hip portion 26, which hip portion 26 is disposed adjacent a user's 56 hip 58 when the urine collection bag holder 10 is worn. A leg portion 28 depends from the hip portion 26. The leg portion 28 is configured to rest against a user's 56 thigh 60 when the urine collection bag holder 10 is worn. A pouch 30 is disposed on the leg portion 28 outside surface 22. The pouch 30 is configured to releasably receive a urine collection bag 62. A plastic window 32, disposed upon the pouch 30, enables a pouch interior 34 to be visible. Levels of urine 64 in the urine bag 62 can thereby be periodically checked without the need of removing the urine collection bag 62 from the pouch 30.

The hip portion 26 has an upper edge 36 with a belt opening 38 continuously disposed throughout the upper edge 36. A belt 40 is disposed through the belt opening 38. The belt 40 is fabric. A hook and loop fastener 42 disposed on each of an outer end 44 of the belt 40 operationally engage each other. The belt 40 is devised to be unobtrusive when worn so as to keep a low profile beneath a user's clothes.

A pair of leg straps 46 secure the leg portion 28 to a user's 56 thigh 60. Each of the pair of leg straps 46 passes through each of a pair of leg strap openings 48 disposed on the leg portion 28 along a horizontal axis of each of a top end 27 and a bottom end 29 of the leg portion 28.

A plurality of vertical slits 50 guides a catheter tube 66 to connect with an upper receptacle 61 of the urine collection bag 62 through a tube opening 52 disposed on the leg portion 28 on an opposite of the leg strap opening from the vertical slits 50 when the urine collection bag 62 is disposed within the leg portion 28 pouch 30.

A drainage cap hole 54 is centrally disposed on the leg portion 28 bottom end 29. The drainage cap hole 54 is configured to receive a urine collection bag 62 drainage cap 68 therethrough.

A urine collection bag 62 is therefore easily installed within the urine collection bag holder 10, the necessary tubes readily connected, and urine 64 collected as desired. Equally, the urine collection bag 62 is easily removed from the urine collection bag holder 10, any collected urine 64 readily drained from the bag 62, and the urine collection bag 62 can be quickly reinstalled, as desired.

The urine collection bag holder 10 has been devised to cut a low profile beneath a user's 56 clothes and simultaneously provide comfort when wearing the urine collection bag holder 10.

What is claimed is:

1. A urine collection bag holder comprising:
   a fabric strip comprising:
      an inside surface;
      an outside surface;
      a hip portion, said hip portion including an upper edge having a belt opening continuously disposed along a horizontal axis thereof;
      a leg portion disposed depending from the hip portion, said leg portion having a leg strap opening continuously disposed therethrough along a horizontal axis thereof, said opening proximal to each of a top end and a bottom end of the leg portion;
   a pouch disposed on the leg portion outside surface configured to releasably receive a urine collection bag therein;
   an interior side of the pouch;
   a plastic window disposed upon an exterior surface of the pouch, whereby the pouch interior side is visible;
   a belt having two outer ends whereby the belt opening slidingly receives a portion of the belt therethrough;
   a hook and loop fastener disposed on each outer end of the belt, said hook and loop fastener disposed on each belt outer end to operationally engage each other around a user's torso;
   a pair of leg straps whereby each of the leg strap openings slidingly receive one of the leg straps therethrough and said leg straps are configured to secure the leg portion to a user's thigh;
   a plurality of vertical slits disposed along a horizontal axis of the leg portion top end;
   a tube opening disposed in the leg portion;
   wherein a catheter tube continuously slidingly extends through the slits and the tube opening and terminates in an upper receptacle of the urine collection bag.

2. The urine collection bag holder of claim 1 further comprising:
   a drainage cap hole centrally disposed on the leg portion bottom end;
   wherein the drainage cap hole is configured to receive a urine collection bag drainage tube therethrough.

3. The urine collection bag holder of claim 2 wherein the belt is fabric.

4. The urine collection bag holder of claim 3 wherein the pouch is made of fabric.

* * * * *